United States Patent
Edelson et al.

(10) Patent No.: US 7,109,031 B2
(45) Date of Patent: *Sep. 19, 2006

(54) METHODS FOR INDUCING THE DIFFERENTIATION OF MONOCYTES INTO FUNCTIONAL DENDRITIC CELLS AND IMMUNOTHERAPEUTIC COMPOSITIONS INCLUDING SUCH DENDRITIC CELLS

(75) Inventors: Richard Leslie Edelson, Westport, CT (US); Carole Berger, Bronx, NY (US); Douglas Hanlon, Branford, CT (US); Michael Girardi, Madison, CT (US)

(73) Assignee: Yale University, New Haven, CT (US)

( * ) Notice: Subject to any disclaimer, the term of this patent is extended or adjusted under 35 U.S.C. 154(b) by 389 days.

This patent is subject to a terminal disclaimer.

(21) Appl. No.: 10/388,716

(22) Filed: Mar. 13, 2003

(65) Prior Publication Data

US 2003/0219420 A1 Nov. 27, 2003

Related U.S. Application Data (63) Continuation-in-part of application No. 10/066,021, filed on Jan. 31, 2002, now abandoned, which is a continuation-in-part of application No. 09/294,494, filed on Apr. 20, 1999, now abandoned.

(51) Int. Cl.
*C12N 5/00* (2006.01)

(52) U.S. Cl. .................... 435/377; 435/366; 435/325; 604/4.01; 604/5.01

(58) Field of Classification Search ................ 435/325, 435/366, 377; 604/4.01, 5.01
See application file for complete search history.

(56) References Cited

U.S. PATENT DOCUMENTS

| | | | |
|---|---|---|---|
| 4,321,919 A | 3/1982 | Edelson | 128/214 |
| 4,398,906 A | 8/1983 | Edelson | 604/6 |
| 4,428,744 A | 1/1984 | Edelson | 604/6 |
| 4,464,166 A | 8/1984 | Edelson | 604/6 |
| 4,612,007 A | 9/1986 | Edelson | 604/5 |
| 4,613,322 A | 9/1986 | Edelson | 604/6 |
| 4,683,889 A | 8/1987 | Edelson | 128/395 |
| 4,684,521 A | 8/1987 | Edelson | 424/101 |
| 4,838,852 A | 6/1989 | Edelson et al. | 604/4 |
| 5,114,721 A | 5/1992 | Cohen et al. | 424/534 |
| 5,462,733 A | 10/1995 | Edelson et al. | 424/93.71 |
| 5,820,872 A | 10/1998 | Edelson et al. | 424/277.1 |
| 6,524,855 B1 | 2/2003 | Edelson et al. | |

FOREIGN PATENT DOCUMENTS

| | | |
|---|---|---|
| WO | WO 93/20185 | 10/1993 |
| WO | WO 94/11016 | 5/1994 |
| WO | WO 97/34472 | 9/1997 |
| WO | WO 99/38380 | 8/1999 |

OTHER PUBLICATIONS

International Search Report of PCT Application No. PCT/US04/07774 Dated Mar. 28, 2005.
Written Opinion of the International Searching Authority issued on PCT/US04/07774 Dated Mar. 28, 2005.
Berger, et al. Induction of Human Tumor-Loaded Dendritic Cells, In. J. Cancer: 2001, pp. 438-447.
Edelson, Light-Activated Drugs, Scientific American, Aug. 1988, pp. 68-75.
UVAR™ Photopheresis System, undated.
PCT Notification of Transmittal of the International Search Report, dated Aug. 9, 2000.
Notes form PCT/USA/220.
Isolation and Function of Human Dendritic Cells: Isolation and Culture from Precursors, p. 821-837 by Ron Jaffe; Copyright 1993.
Dendritic Cells: Origin and Differentiation by Rajeny Thomas, et al., Accepted for publication Oct. 30, 1995.
Article published in The Journal of Immunology, entitled—TGF-B1 Promotes In Vitro Generation of Dendritic Cells, etc. by Elisabeth Riedl, et al. vol. 158/Np4/Feb. 15, 1997.
Article published in The Journal of Immunology, entitled—TGF-B1 Promotes In Vitro Development of Dendritic Cells, etc. by Herbert Strobl, et al. dated Aug. 15, 1996.
Contrasting Effects of IL-4 and CD40 Ligan on the In Vitro Differentiation of Human Dendritic Cells, etc. by B. Canque, et al., date Nov. 15, 1997, published in *Blood* Magazine, vol. 90, No. 10 Supplement 1 (Part 1 of 2).
Abstract #668 from an article entitled: Transforming Growth Factor, etc. published in *Blood* Magazine by A. Garbe, et al., dated Nov. 15, 1998, vol. 92, No. 10 Supplement 1 (Part 1 of 2).
flt3 Ligand in Cooperation with Transforming Growth factor, et c. by Herbert Strobl, et al. published in *Blood* Magazine, vol. 90, No. 4, dated Aug. 15, 1997.

*Primary Examiner*—L. Blaine Lankford
(74) *Attorney, Agent, or Firm*—McCarter & English, LLP.

(57) ABSTRACT

A method for inducing differentiation of monocytes contained in an extracorporeal quantity of a subject's blood into functional dendritic antigen presenting cells is provided. The monocytes are induced to differentiate into dendritic cells by activation forces resulting from flow of the monocytes through a treatment apparatus having plastic channels. The interior surface of the plastic channel may be modified to increase the available surface area for interaction with blood monocytes. Platelets and serum protein may be removed from the blood prior to treatment to reduce or eliminate contamination of the plastic channel by these blood components. Functional dendritic cells generated from induced monocytes are incubated together with apoptotic or inactivated disease effector agents to enhance the presentation of at least one disease-causing antigen expressed by the disease effector agents. Compositions including dendritic cells derived from induced monocytes and compositions including such dendritic cells incubated with disease effector agents are also provided for use in immunotherapeutic treatment.

29 Claims, 6 Drawing Sheets

METHODS FOR INDUCING THE DIFFERENTIATION OF MONOCYTES INTO FUNCTIONAL DENDRITIC CELLS AND IMMUNOTHERAPEUTIC COMPOSITIONS INCLUDING SUCH DENDRITIC CELLS

The present application is a continuation-in-part of patent application Ser. No. 10/066,021 filed on Jan. 31, 2002, which is a continuation-in-part of patent application Ser. No. 09/294,494 filed on Apr. 20, 1999, now abandoned.

FIELD OF THE INVENTION

The present invention relates to improved methods for inducing the differentiation of monocytes into functional dendritic antigen presenting cells and, more particularly, to extracorporeal methods for treating and incubating monocytes to induce such differentiation. The present invention further provides methods for producing immunotherapeutic compositions including these dendritic cells. In particular, the present invention provides immunotherapeutic compositions comprising functional dendritic cells derived from induced monocytes presenting at their surface antigens from apoptotic or inactivated disease effector agents.

BACKGROUND OF THE INVENTION

The use of dendritic cells in cancer immunotherapy is presently an area of significant clinical inquiry. Dendritic cells are highly effective in presenting antigens to responding T-cells; however, dendritic cells normally constitute less than one percent of blood mononuclear leukocytes. Accordingly, a number of in vitro methods have been developed to expand populations of dendritic cells to augment anti-cancer immunity. By exposing increased numbers of dendritic cells to antigens on tumor or other disease-causing cells, followed by reintroduction of the antigen-loaded dendritic cells to the patient, presentation of these antigens to responding T-cells can be enhanced significantly.

For example, culturing blood mononuclear leukocytes for eight days in the presence of granulocyte-monocyte colony stimulating factor (GM-CSF) and interleukin-4 (IL-4) produces large numbers of dendritic cells. These cells can then be externally loaded with tumor-derived peptide antigens for presentation to T-cells. Alternatively, the dendritic cells can be transduced to produce and present these antigens themselves. Expanding populations of dendritic cells transduced to produce and secrete cytokines which recruit and activate other mononuclear leukocytes, including T-cells, may be an even more effective method of generating anti-tumor immune responses.

Transducing cultivated dendritic cells to produce a particular generic tumor antigen and/or additional cytokines is labor intensive and expensive. More importantly, this procedure likely fails to produce and present those multiple tumor antigens that may be most relevant to the individual's own cancer. Several approaches have been proposed to overcome this problem. Hybridization of cultivated autologous dendritic cells with tumor cells would produce tetraploid cells capable of processing and presenting multiple unknown tumor antigens. In a second proposed approach, acid elution of Class I and Class II major histocompatability complexes (MHC) from the surface of malignant cells would liberate a broad spectrum of tumor-derived peptides. These liberated peptides could then be externally loaded onto MHC complexes of autologous cultivated dendritic cells.

Conventional photopheresis is a method of vaccinating patients against leukemic lymphocytes, even when the distinctive tumor antigen(s) is not known. In this method, malignant cells are exposed to photo-activated 8-methoxypsoralen (8-MOP) which enhances cell surface display of Class I MHC-associated tumor antigens. After intravenous return of these altered malignant lymphocytes to the original patient, a potent anti-tumor response may be generated in about 25% of the patients, leading to diminution of the malignant cell population and occasionally long-standing remissions. Experimental studies in mice, in which autologous dendritic cells are first grown in tissue culture and then admixed with the 8-MOP-treated tumor cells, appears to increase the efficacy of conventional photopheresis. In this experimental protocol, tumorigenic mouse T-cells are rendered apoptotic by photopheresis using 8-MOP and exposure to ultraviolet (UV) energy. Following this chemical alteration of the malignant leukocytes, autologous cultured dendritic cells are added to the apoptotic T-cells, and the cell mix is incubated overnight with shaking to maximize contact between the T-cells and the dendritic cells. The apoptotic T-cell/dendritic cell mix has proven to be an effective cellular vaccine in test mice challenged with viable tumorigenic 2B4.11 cells.

While the above-described experimental protocol is apparently more efficient and comprehensive than alternative approaches, it requires extensive ex vivo cellular manipulations over a period of several days. Accordingly, an in vivo procedure which could in a single day provide large numbers of functional dendritic cells and expose those cells to apoptotic tumor cells would greatly simplify the means by which the anti-tumor cellular vaccine could be prepared.

SUMMARY OF THE INVENTION

The present invention is based on the convergence of two disparate phenomena: treating monocytes in a manner which induces their differentiation into functional dendritic antigen presenting cells, and treating disease effector agents, such as tumor cells, to render them apoptotic or to inactivate them. By incubating these treated populations together for a period of time sufficient to optimize processing and presentation by the dendritic cells of disease associated antigens distinctive to the disease effector agents, prior to returning the dendritic antigen presenting cells to the patient, clinically enhanced immunity to the disease associated antigens is achieved. Alternatively, monocytes may be treated to induce differentiation and returned to the subject where they may come into physical contact with malignant tumor cells in vivo.

As used herein, the term "disease effector agents" refers to agents that are central to the causation of a disease state in a subject and which express disease-associated antigens. In certain circumstances, these disease effector agents are disease-causing cells which may be circulating in the bloodstream, thereby making them readily accessible to extracorporeal manipulations and treatments. Examples of such disease-causing cells include malignant T-cells, malignant B cells, T-cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells can be manipulated extracorporeally in analogous fashion to blood leukocytes, after they are brought into suspension or propagated in tissue culture. Alternatively, in some instances, it has been shown that the circulating blood of patients with solid tumors can contain malignant cells that have broken off from the tumors and entered the circulation. [Kraeft, et al., Detection and analysis of cancer cells in blood and bone marrow using a rare event imaging system, *Clinical Cancer Research*, 6:434–42, 2000.] These circulating tumor cells can provide an easily accessible source of cancer cells which may be rendered apoptotic and presented to the dendritic cells formed by the method described and claimed herein.

In addition to disease-causing cells, disease effector agents falling within the scope of the invention further include microbes such as bacteria, fungi and viruses which express disease-associated antigens. It should be understood that viruses can be engineered to be "incomplete", i.e., produce distinguishing disease-causing antigens without being able to function as an actual infectious agent, and that such "incomplete" viruses fall within the meaning of the term "disease effector agents" as used herein. It should also be understood that numerous treatments may be used for inactivation of viruses by both physical means and through the use of substances. For example, one well recognized method for inactivating viruses, as well as for rendering virally infected cells apoptotic, is by the use of light activated substances, such as for example photoactivated 8-methoxypsoralen (8-MOP), the pharmacologic agent regularly used in Photopheresis.

While use of a photochemical agent such as 8-MOP is one known method for inactivation of viruses, there are many other treatments to inactivate viruses, involving either other photoactivatable chemicals or other methods, which were well known to those skilled in the art at the time that the parent of the present application was filed. For example, hypericin is effective in inactivating a broad range of viruses in blood and blood components. Other treatments for inactivation of viruses include, for example, treatments using ozone. Also, a variety of chemical disinfectants are known to inactivate viruses. An example of yet another treatment for inactivating viruses is through the use of antibodies, as described, for example, in McCullough, K. C. et al., Opsonization-enhanced phagocytosis of foot-and-mouth disease virus, *Immunology*, 65(2):187–91 (1988). Antibodies against specific types of viruses are very well known to bind to and inactivate the viruses, while forming complexes with the inactivated viruses which are readily taken up by antigen presenting cells, such as dendritic cells. The Fe portion of the antibodies bind to Fe receptors on dendritic cells, thereby "opsonizing" the viral antigens for uptake and processing by the dendritic cells.

Because dendritic cells will internalize the inactivated virus regardless of the method by which the virus is inactivated, inactivation by any method known to those skilled in the art will put the virus in condition to be internalized by dendritic cells.

The present invention provides methods for treating an extracorporeal quantity of a patient's blood to induce the differentiation of monocytes contained in the blood into functional antigen presenting dendritic cells. In one embodiment of the present invention, the extracorporeal quantity of the patient's blood is treated using a conventional photopheresis apparatus to induce differentiation of the monocytes into dendritic cells. While not wishing to be limited to any particular mechanism, the inventors believe that monocytes in the blood are attracted to and stick to the plastic surfaces of the channels in the photopheresis apparatus, and they are subsequently released from the plastic surfaces by shearing forces from the flow of fluid through the channel. Thus, as the monocytes pass through the photopheresis apparatus, they undergo sequential adherence to and release from the plastic surface. The physical forces of these events send activation signals through the cell membrane and induce the monocytes to differentiate into functional dendritic cells.

In another embodiment of the present invention, monocyte differentiation is induced by pumping a blood leukocyte preparation containing monocytes through a plastic treatment apparatus. The plastic treatment apparatus may be comprised of any plastic material to which blood monocytes will transiently adhere and that is biocompatible with blood leukocyte cells. Within the plastic treatment apparatus are narrow plastic channels, and the blood leukocytes flow through the narrow plastic channels. The monocytes contained in the blood leukocyte preparation sequentially adhere to, and are released from, the plastic surfaces as described above. The interior surfaces of the treatment apparatus may be modified to increase the plastic surface area to which the monocytes are exposed as they flow through the plastic treatment device. The surface area may be increased by mechanical means, such as by etching the surface or blasting the surface with silica, plastic or metal beads, or by forming the plastic with grooves or other means for increasing the surface area.

Monocyte differentiation into functional dendritic cells may also be enhanced by removing plasma and serum proteins from the blood leukocyte preparation prior to passing the monocyte through the plastic treatment apparatus. The plasma and blood proteins can adhere to the plastic surface of the treatment apparatus, preventing adhesion of monocytes. By reducing or eliminating plasma and serum proteins from the blood leukocyte preparation, the plastic surface area for monocyte interaction is increased, thereby increasing the number of functional dendritic cells produced.

After treatment of the leukocytes to induce monocyte differentiation, the functional dendritic cells are incubated in the presence of apoptotic disease effector agents to allow the dendritic cells to phagocytize the disease effector agents and present antigens from the disease effector agents to T-cells in a subject's immune system. In a particularly preferred embodiment of the present invention, as the blood is passed through a photopheresis apparatus to induce differentiation of monocytes into functional dendritic cells, disease effector agents in the blood are rendered apoptotic by treating the disease effector agents with a photoactivatable substance and irradiating the blood as it passes through the photopheresis apparatus. By rendering the disease effector agents apoptotic as the monocytes are induced to form new dendritic cells, the method of the present invention results in an enhanced number of antigen presenting dendritic cells which can be reinfused into the patient to trigger an immunotherapeutic response.

In this embodiment of the invention, after the extracorporeal quantity of blood has been treated in the photopheresis device, the treated blood is incubated for a period of from about 6 to about 48 hours, most preferably from about 12 to about 24 hours. During this period, the dendritic cells phagocytize the apoptotic disease effector agents and present antigens from the phagocytized cells at their surface, where they will be recognized by T-cells in the patient's immune system, thereby inducing an immunological response to the disease effector agents in the patient.

In another embodiment of the present invention, which is particularly effective in treating malignant T-cells contained in the blood, the disease effector agents in the blood are rendered apoptotic using monoclonal antibodies. The monoclonal antibodies may include a free $F_c$ segment at the end of the antibody, which can bond with a complementary receptor on the surface of the dendritic cells. The antibodies thus form bridges between the apoptotic disease cells and the dendritic cells, increasing the likelihood that the apoptotic cells will be phagocytized and processed by the dendritic cells. Alternatively, the disease effector cells can be rendered apoptotic by other methods, and coated with monoclonal antibodies with available $F_c$ receptors to enhance uptake and processing of apoptotic disease effector agents by the functional dendritic cells. Also, non-apoptotic disease effector agents, such as cancer cells from solid tumors which have broken off and are circulating in the blood, may be coated with antibodies to enhance uptake of the cancer cells by functional dendritic cells.

DETAILED DESCRIPTION OF THE INVENTION

As noted above, monocyte differentiation is initiated by exposing the monocytes contained in an extracorporeal quantity of a subject's blood to the physical forces resulting from the sequential adhesion and release of the monocytes on plastic surfaces, such as the surfaces of the channels of a conventional photopheresis device. In one embodiment of the invention, a white blood cell concentrate is prepared in accordance with standard leukapheresis practice using a leukapheresis/photopheresis apparatus of the type well known to those skilled in the art. The white blood cell concentrate includes monocytes, lymphocytes and some red blood cells and platelets. Typically, up to two billion white blood cells are collected during leukapheresis. Assuming that monocytes comprise from about 2% to about 50% of the total white blood cell population collected, approximately 40 million to 1 billion monocytes are present in the white blood cell concentrate.

Following separation by leukapheresis, monocyte differentiation is induced by pumping the blood cell concentrate through a device which has a plurality of plastic channels. Preferably, the plastic channels have a diameter of between about 0.5 mm and 5.0 mm. Most preferably, a conventional photopheresis apparatus having a channel diameter of 1 mm or less is used. The narrow channel configuration of the photopheresis apparatus maximizes the surface area of plastic to which the blood cell concentrate is exposed as it flows through the photopheresis apparatus. The invention is not limited in this regard, however, and any appropriate device having plastic channels may be used to induce monocyte differentiation.

Treatment Using Conventional Photopheresis Apparatus

In one embodiment of the present invention wherein the blood cell concentrate is treated using a photopheresis apparatus, monocyte differentiation is induced by the physical forces experienced by the monocytes as they flow through the plastic channels in the photopheresis apparatus. While the invention is not limited to any particular mechanism, the inventors believe that monocytes in the blood cell concentrate are attracted to the plastic channel walls of the photopheresis apparatus, and the monocytes adhere to the channel walls. The fluid flow through the channel imposes shearing forces on the adhered monocytes that cause the monocytes to be released from the plastic channel walls. Accordingly, as the monocytes pass through the photopheresis apparatus, they may undergo several episodes of adherence to and release from the plastic channel walls. These physical forces send activation signals though the monocyte cell membrane, which results in induction of differentiation of monocytes into immature dendritic cells that are aggressively phagocytic.

Inducing monocytes to form dendritic cells by this method offers several advantages for immunotherapeutic treatment. Because all of the dendritic cells are formed from the monocytes within a very short period of time, the dendritic cells are all of approximately the same age. Dendritic cells will phagocytize apoptotic cells during a distinct period early in their life cycle. In addition, the antigens present in the phagocytized apoptotic cells are processed and presented at the surface of the dendritic cells during a later distinct period. By creating dendritic cells with a relatively narrow age profile, the method of the present invention provides an enhanced number of dendritic cells capable of phagocitizing apoptotic disease effector agents and subsequently presenting antigens from those disease effector agents for use in immunotherapeutic treatment.

Following treatment to initiate differentiation of monocytes, the treated blood cell concentrate is sequestered for incubation in the presence of apoptotic or inactivated disease effector agents. The incubation period allows the dendritic cells forming and maturing in the blood concentrate to be in relatively close proximity to the apoptotic disease effector agents, thereby increasing the likelihood that the apoptotic disease agents will be consumed and processed by the dendritic cells. As described below, the disease cells may be induced to apoptosis as the blood concentrate is being passed through the photopheresis apparatus, or the disease cells may be treated separately to induce apoptosis and added to the blood concentrate before or after passage of the blood concentrate through the photopheresis device. A standard blood bag may be utilized for incubation of the cells, as is typical in photopheresis. However, it has been found to be particularly advantageous to use a blood bag of the type which does not leach substantial amounts of plasticizer and which is sufficiently porous to permit exchange of gases, particularly $CO_2$ and $O_2$. Such bags are available from, for example, the Fenwall division of Baxter Healthcare Corp. under the name Amicus™ Apheresis Kit. Various plasticizer-free blood bags are also disclosed in U.S. Pat. Nos. 5,686,768 and 5,167,657, the disclosures of which are herein incorporated by reference.

The blood cell concentrate and disease effector cells are incubated for a period of time sufficient to maximize the number of functional antigen presenting dendritic cells in the incubated cell population. Typically, the treated blood cell concentrate and disease effector cells are incubated for a period of from about 6 to about 48 hours, with the preferred incubation time extending over a period of from about 12 to about 24 hours. By treating monocytes in the manner described above and then incubating the treated cell population, a large number of functional antigen presenting dendritic cells can be obtained. The activated monocytes produce natural cytokines which aid in the differentiation of the monocytes into dendritic cells. Alternatively, a buffered culture medium may be added to the blood bag and one or more cytokines, such as GM-CSF and IL-4, during the incubation period.

In a preferred embodiment of the present invention, which is particularly useful where the disease effector agent is circulating in the subject's blood, such as for example when the disease effector cells are malignant T-cells, the disease effector agents are rendered apoptotic in the photopheresis apparatus as the monocytes are induced to form dendritic cells by the physical forces they experience in the photopheresis apparatus. A photoactivatable agent capable of inducing apoptosis in the disease effector cells is added to the blood cell concentrate prior to passage through the photopheresis apparatus, and the blood cell concentrate is irradiated as it passes through the photopheresis apparatus to render the disease cells apoptotic. By rendering the disease cells apoptotic in the photopheresis apparatus, these cells are immediately available to be phagocytized as the monocytes are differentiating to form dendritic cells.

In this embodiment of the present invention, saline is added to the white blood concentrate prior to photopheresis to dilute the red blood cell concentration to about 2% by volume, thereby permitting more effective penetration of the activating radiation to the target disease cells. The photoactivatable agent can be administered to the subject prior to obtaining a quantity of blood from the subject for leukapheresis and photopheresis. Alternatively, or additionally, the photoactivatable agent can be added directly to the extracorporeal bloodstream, typically by injecting the agent into the tubing leading to the leukapheresis/photopheresis apparatus. Regardless of when and how a particular agent is administered, the disease cells must be exposed to the photoactivatable agent for a period of time sufficient for the agent to react with cellular components in the disease cells.

Exemplary photoactivatable agents which may be used in the present invention are psoralens, porphyrins, pyrenes, phthalocyanine, retinoid derivatives, photoactivated cortisone, photoactivatable dyes, and monoclonal antibodies which have been linked to porphyrin molecules. The invention is not limited in this regard, and any appropriate photoactivatable agent known to those skilled in the art may be used.

The psoralens are a preferred class of photoactivatable agents for use in the photopheresis procedure. Psoralens are readily absorbed from the digestive track, reaching peak levels in the blood and other tissues in one to four hours following oral administration, and these agents are excreted almost entirely within 24 hours. Accordingly, the psoralens are particularly suitable for oral administration prior to obtaining an extracorporeal quantity of the subject's blood. The psoralen molecules are inert prior to exposure to irradiation and are transiently activated to an excited state following irradiation. The preferred psoralens include 8-methoxypsoralen (8-MOP), 4' aminomethyl-4, 5', 8 trimethyl-psoralen (AMT), 5-methoxypsoralen (5-MOP), and trimethyl-psoralen (TMP). 8-MOP is the most preferred photoactivatable agent for use with the methods of the invention, and the conditions for oral administration of this psoralen are described in U.S. Pat. No. 5,147,289, the disclosure of which is incorporated herein by reference.

The irradiation stage of photopheresis is performed as the blood cell concentrate is passed through the photopheresis apparatus. The preferred exposure device includes a transparent plastic channel having a diameter of about 1 mm disposed between opposed irradiation sources. Referring again to the preferred embodiment, as the blood cell concentrate passes through the plastic channel, the disease cells are never separated from the irradiation sources by more than about 0.5 mm of blood. Maintaining the disease cells in such close proximity to the irradiation sources has proven particularly effective in ensuring adequate exposure of the disease cells to the activating radiation. In the case where a psoralen such as 8-MOP is used as the photoactivatable agent, the irradiation sources emit ultraviolet A radiation (UVA) as the activating radiation. To activate the psoralen, the treated disease cells are typically exposed to about 1–2 joules/cm$^2$ of UVA for a period of from about 15 to about 150 minutes.

Figure 2:
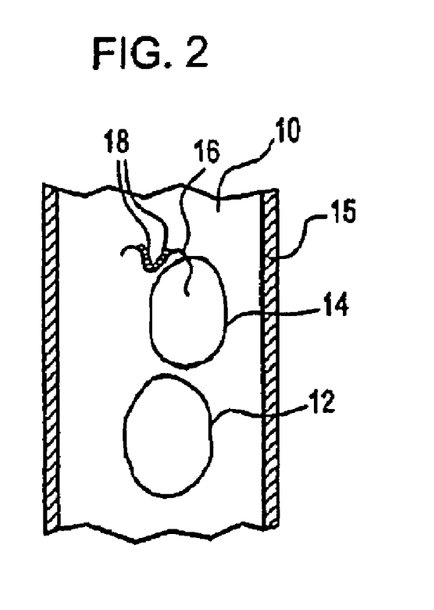
FIG. 2 is a cross-sectional view of a plastic channel containing the subject's blood illustrating a CTCL cell with a class I associated peptide antigen and a blood monocyte.

The application of one embodiment of the method described above is illustrated in FIGS. 2–10 for the treatment of a particular type of cancer called Cutaneous T-Cell Lymphoma (CTCL). FIGS. 2–10 illustrate treatment of individual cells, but it should be understood that in practice the subject's blood will contain a plurality of the various cells described below, and that the plurality of cells are treated simultaneously. Referring to FIG. 2, a plastic channel 10 contains a quantity of the subject's blood, or the blood cell concentrate if the subject's blood is first treated by leukapheresis. The blood contains blood monocytes 12 and malignant CTCL cells 14. The malignant CTCL cells display class 1 associated peptide antigens 16 comprised of a plurality of amino acids 18. The subject's blood is pumped through the plastic channel to induce differentiation of the monocytes into dendritic cells.

Figure 3:
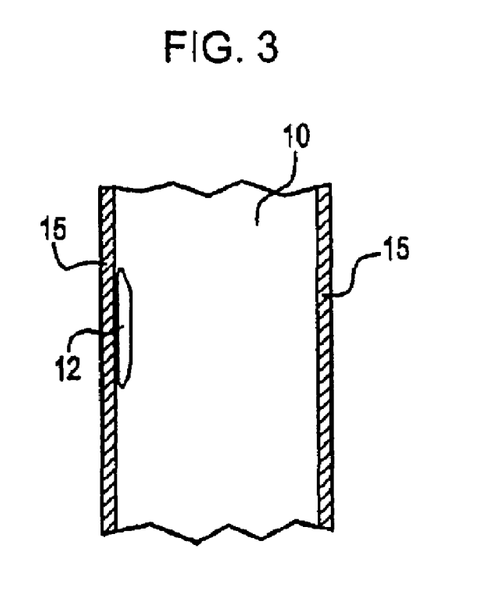
FIG. 3 is a cross-sectional view of a plastic channel containing the subject's blood illustrating a blood monocyte adhered to the wall of the plastic channel.
Figure 4:
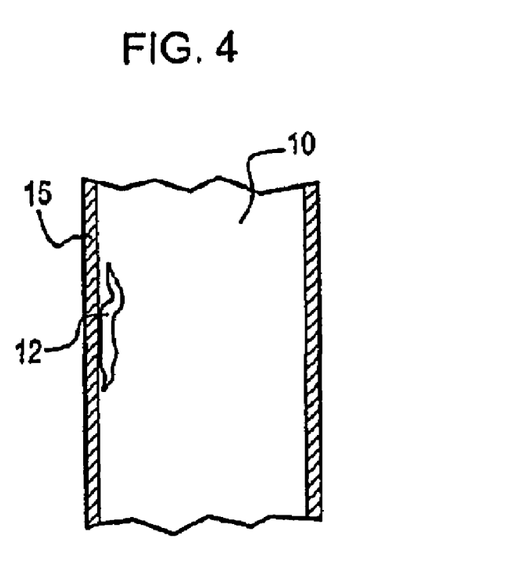
FIG. 4 is a cross-sectional view of a plastic channel containing the subject's blood illustrating a blood monocyte partially adhered to the wall of the channel.
Figure 5:
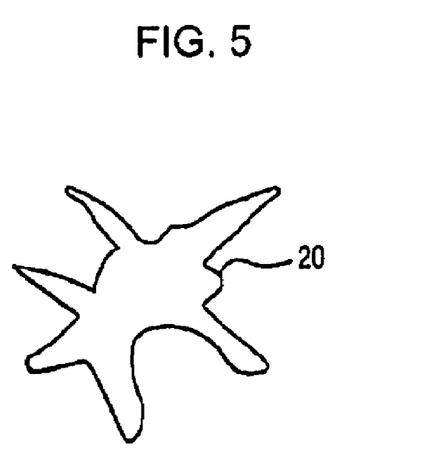
FIG. 5 is an illustration of dendritic cell produced by differentiation of a blood monocyte by the method of the present invention.

As shown in FIG. 3, as the subject's blood is pumped though the plastic channel, monocytes 12 adhere to the walls 15 of the plastic channel 10. Shear forces are imposed on the adhered monocytes by the fluid flowing past the monocytes and, as shown in FIG. 4, the monocytes 12 become dislodged from the wall 15. As the monocytes flow through the plastic channel, they may undergo several episodes of adherence and removal from the channel walls. As a result of the forces experienced by the monocyte, activation signals are transmitted which cause the monocyte to differentiate and form an immature dendritic cell 20, illustrated in FIG. 5.

Figure 6:
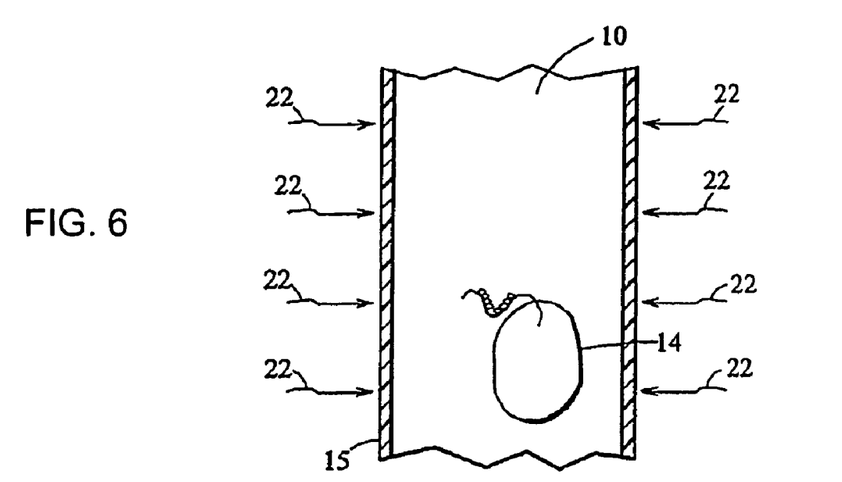
FIG. 6 is a cross-sectional view of a plastic channel illustrating a CTCL cell with a class 1 associated peptide antigen being irradiated to render the CTCL apoptotic.

As discussed above, in a particularly preferred embodiment, the plastic channel is part of a conventional photopheresis apparatus. This allows the malignant CTCL cells to be rendered apoptotic as the blood is passed through the plastic channels. The subject's blood is treated prior to passage though the channels with a photoactivatable agents, such as 8-MOP. As illustrated in FIG. 6, as the treated CTCL cell 14 passes though the plastic channel 10 of the photopheresis device (not shown), ultraviolet light 22 is transmitted though the transparent plastic channel walls 15 of the photopheresis apparatus. The ultraviolet light 22 activates the photoactivatable agent, thereby inducing apoptosis of the malignant CTCL cell 14.

Figure 7:
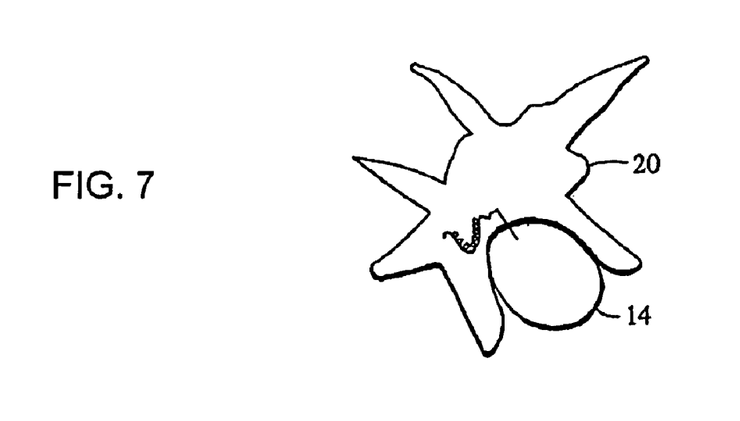
FIG. 7 is an illustration of an apoptotic CTCL cell in the process of being phagocytized by a dendritic cell.
Figure 8:
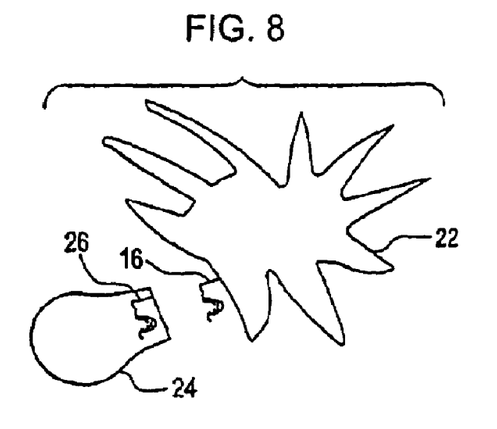
FIG. 8 is an illustration of a dendritic cell which has been reinfused into the subject's bloodstream presenting the class 1 associated peptide antigen to a T-cell.

After the blood has been passed though the photopheresis apparatus, the subject's blood is incubated to allow phagocytization of the apoptotic CTCL cells and subsequent maturation of the dendritic cells. As illustrated in FIG. 7, the dendritic cell 20 ingests the apoptotic CTCL cell 14 during the incubation period. As the dendritic cell continues to mature during the incubation period, it processes the apoptotic malignant CTCL cell. As shown in FIG. 8, at the end of the incubation period, after the dendritic cell digests the malignant CTCL cell, the associated class I peptide antigen 16 is presented at the surface of the dendritic cell 20. After the incubation period, the composition containing the antigen presenting dendritic cells is reinfused into the subject for immunotherapy.

Figure 9:
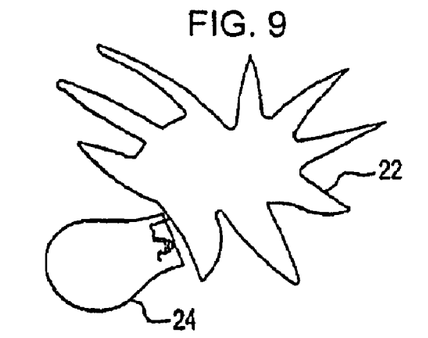
FIG. 9 is an illustration of the class 1 associated peptide antigen presented on the surface of the dendritic cell as it is received by a complementary receptor site on the T-cell.
Figure 10:
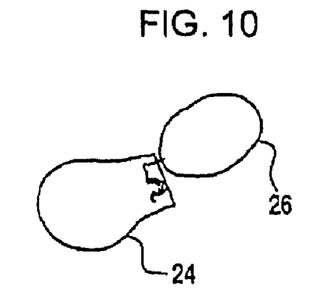
FIG. 10 is an illustration of a clone of the activated T-cell attacking a CTCL cell displaying the class 1 associated peptide antigen.

Referring now to FIGS. 8 and 9, which illustrate the antigen presenting dendritic cell after reinfusion into the subject's blood stream, the dendritic cell 22 presents at its surface the class 1 peptide antigen 16 from the malignant CTCL cell to a healthy T-cell 24 which has a receptor site 26 for the class 1 peptide antigen. When the healthy T-cell 24 receives the class 1 peptide antigen from the dendritic cell, as shown in FIG. 9, the healthy T-cell is activated and induces the formation of T-cell clones which will recognize and attack malignant T-cells displaying the same class 1 peptide antigen. As a result, as shown in FIG. 10, the healthy T-cell clones 24 of the subject's immune system are triggered to recognize the class I peptide antigen displayed by the malignant CTCL cell clones, and to attack and kill malignant CTCL cell clones 28 in the subject which display the same class 1 peptide antigen.

While the foregoing description refers to the method for treating CTCL, it should be understood that the invention is not limited in this regard, and the method may be used to treat other types of cancer or disease. In addition, as described further herein, the method can be performed using any type of device having plastic channels to induce monocyte differentiation. Moreover, the cancer cells or other disease effector agents can be rendered apoptotic by any method known to those skilled in the art and incubated with the dendritic cells formed by the method of the present invention.

As described above, by inducing apoptosis in disease cells in the photopheresis apparatus at the same time that monocytes are induced to differentiate into dendritic cells, the dendritic cells are more likely to phagocytize the disease cells and present antigens from the disease cells for use in immunotherapeutic treatment. This embodiment of the invention is particularly useful when the disease effector agents are present in the subject's blood, such as, for example, where the disease cells are malignant T-cells. This embodiment of the invention may also be used where the disease cells are cells from a solid tumor. It has been shown that, in at least some cases, cells from solid tumors can break off and circulate in the blood. Under these circumstances, it may be preferable to induce apoptosis of the tumor cells in the photopheresis apparatus at the same time that monocytes undergo differentiation into dendritic cells.

In another embodiment of the present invention, the disease effector agents in the subject's blood are coated with monoclonal antibodies which selectively bind to the surface of the disease cell. The bound monoclonal antibodies are long chained proteins which include a free $F_c$ segment at the end of the protein chain. As described in Dhodapker et al., [Antitumor monoclonal antibodies enhance cross-penetration of cellular antigens and the generation of myeloma-specific killer T cells by dendritic cells, *Journal of Experimental Medicine*, 195:125–33, 2002], the monoclonal antibodies attach to the disease cells, and the free $F_c$ segment is attracted to, and bonds with, a complementary receptor on the surface of the dendritic cell. This bond between the $F_c$ segment on the monoclonal antibody and complementary receptor on the dendritic cell essentially forms a bridge to the apoptotic disease effector cell, thereby increasing the likelihood and speed of the uptake of the apoptotic disease effector cells by the dendritic cells. The antibodies also appear to direct the ingested cancer antigens to a pathway which culminates in the antigens stimulating a CD8 antitumor immune response. Preferably, the disease effector agent is rendered apoptotic prior to being coated with the monoclonal antibodies. The invention is not limited in this regard, however, monoclonal antibodies may be used to enhance uptake and processing of non-apoptotic disease effector agents.

The method of the present invention may be used, for example, for immunotherapeutic treatment of subjects having solid tumors without the need for invasive procedures to obtain cancer cells. In some instances, the circulating blood of patients with solid tumors may contain cancer cells that have broken off from the tumors and entered the circulation. [Kraeft, et al., Detection and analysis of cancer cells in the blood and bone marrow using a rare event imaging system, Clinical Cancer Research, 6:434–42, 2000]. These circulating cancer cells may be present in the circulating blood at relatively low levels, as little as 10–100 cancer cells per million cells. Antibodies which react with specific types of cancer cells, and do not react with white blood cells, can be added to the blood to bind with the cancer cells. Such antibodies which distinguish and bind to particular types of cancer cells are well known to those skilled in the art. The free segment at the end of the antibody protein chain preferentially bonds to a complementary receptor site on the dendritic cell. Thus, the antibodies bound to the cancer cells can preferentially direct the cancer cells to dendritic cells, thereby enhancing uptake of the cancer cells by the dendritic cells. This procedure can eliminate the need to remove the cancer cells from the patient prior to treatment, as the antibodies act to direct those cancer cells present in the blood to the dendritic cells. The cancer cells are preferably rendered apoptotic prior to coating with the antibody, but the invention is not limited in this regard, and non-apoptotic cancer cells may be used.

In the case of cutaneous T-cell lymphoma, coating the malignant T-cells with monoclonal antibodies induces apoptosis of the T-cells, increases the uptake of the dying T-cells by the dendritic cells, and increases the rate of processing of the T-cell antigens by the dendritic cells. Monoclonal antibodies may also be used with other types of disease causing cells, such as cancer cells or disease causing T and B lymphocytes (such as in autoimmune disorders, organ transplant rejection and graft versus host disease following stem cell transplants), to increase the uptake and processing of the cancer cells by the dendritic cells. For example, antibodies against breast cancer, colon cancer and prostate cancer are available and could be used to coat the relevant cancer cells. The cancer cells may be rendered apoptotic by any method known to those skilled in the art, and the apoptotic cancer cells can be coated with antibodies having free $F_c$ fragments. The free $F_c$ fragment bonds to the complementary receptor on the dendritic cells, thereby forming a bridge between the dendritic cell and the apoptotic disease effector agent to enhance the uptake and processing of the apoptotic disease cell by the dendritic cell.

Preferably, the disease effector agents are induced to apoptosis and coated with antibodies prior to the passage of the blood through the photopheresis device to induce monocyte differentiation into dendritic cells. Alternatively, the disease effector agents contained in the subject's blood may be induced to apoptosis and coated with antibodies after passage of the blood though the photopheresis apparatus and prior to incubation. If desired, the disease effector agents can be treated separately from the blood cell concentrate which is passed though the photopheresis apparatus and added to the processed blood prior to incubation.

It should also be understood that it is not absolutely necessary to separate the monocytes from the extracorporeal quantity of the patient's blood by leukapheresis prior to treatment. As long as the monocytes contained in the blood are sufficiently exposed to physical forces imposed by flow through plastic channels to initiate differentiation into dendritic cells followed by subsequent incubation, separation of the monocyte population is not required.

Inducing monocyte differentiation according to the invention provides dendritic cells in numbers which equal or exceed the numbers of dendritic cells that are obtained by expensive and laborious culture of leukocytes in the presence of cytokines such as GM-CSF and IL-4 for seven or more days. The large numbers of functional dendritic cells generated by the method of the present invention provide a ready means of presenting selected disease associated antigens and are thereby conducive to efficient immunotherapy. Antigen preparations selected to elicit a particular immune response and derived from, for example, tumors, disease-causing non-malignant cells, or microbes such as bacteria, viruses and fungi, can be added directly to the blood bag during incubation. The microbes may preferably be inactivated by prior exposure to 8-MOP or other agents. It is known that 8-MOP can cause apoptosis in bacteria and fungi and can inactivate viruses. Bringing mature dendritic cells into close contact with such antigen preparations within the confines of the blood bag provides large numbers of antigen-loaded dendritic cells. The antigen-loaded dendritic cells can be used as immunogens by reinfusing the cells into the subject or by otherwise administering the cells in accordance with methods known to elicit an immune response, such as subcutaneous, intradermal or intramuscular injection. As described below, it is also possible to generate antigen-loaded dendritic cells by treating and co-incubating monocytes and disease effector agents which are capable of expressing disease associated antigens.

In another aspect of the present invention, monocytes may be induced to differentiate into functional dendritic cells, and the disease effector agents can be rendered apoptotic or inactive, or may be otherwise treated, separately from the blood or blood cell concentrate used to form the dendritic cells. As discussed above, such disease effector agents comprise microbes, such as bacteria, fungi, and complete and incomplete viruses, and disease-causing clonal populations of cells, including clones of malignant cells or clones of non-malignant T- or B-cells attacking the individual's own tissues or transplanted tissues. Since these agents have distinctive antigens on their surface that permit them to be distinguished from most other cells, immune reactions can be ideally developed against their distinctive antigens. These immune reactions can then suppress or eliminate the disease effector agent populations. Through the generation of dendritic antigen-presenting cells capable of effectively introducing the relevant antigens to a responding immune system, this invention substantially enhances the likelihood of such a disease-controlling immunologic response.

Central to this aspect of the invention is the co-cultivation of increased numbers of antigen presenting dendritic cells, generated as described above, with clones of apoptotic disease-causing cells or inactivated or incomplete microbes which bear distinctive antigens. In the case of disease-causing cells, bacteria and fungi, other means of inducing apoptosis, in addition to exposure to photo-activated drugs, may be applicable.

For example, synthetic peptides with the arginine-glycine-aspartate (RGD) motif could be added to cell suspensions of the disease-causing cells isolated from the patient's blood, from excised solid tumors or tissue cultures of the same. RGD has been shown (*Nature*, Volume 397, pages 534–539, 1999) to induce apoptosis in tumor cells, possibly by triggering pro-capase-3 autoprocessing and activation. Similarly, apoptosis could be induced in cells having Fas receptors, by stimulating with antibodies directed against this receptor, in this way sending signals to the inside of the cell to initiate programmed cell death, in the same way that normally Fas ligand does. In addition, apoptosis can be induced by subjecting disease-causing cells to heat or cold shock, certain viral infections (i.e., influenza virus), bacterial toxins, and x-ray or gamma-irradiation. Alternatively, certain infectious agents such as influenza virus can cause apoptosis and could be used to accomplish this purpose in cell suspensions of disease-causing cells.

Hence, these approaches, although not as usually preferred as the induction of apoptosis by photo-activated 8-MOP, could accomplish the purpose of initiating apoptosis or inactivation in disease-causing cellular populations, prior to their co-cultivation with the induced dendritic antigen-presenting cells and return to the patient for purposes of immunization. Of course, it should be understood that since viruses are not cells, they cannot undergo apoptosis as that term is generally understood and used by those skilled in the art. It is known, however, that viruses can be inactivated by exposure to 8-MOP and other photo-activated drugs and therefore can be treated in this manner prior to their co-cultivation with induced dendritic antigen presenting cells.

Treatment Using Plastic Treatment Apparatus

In another embodiment of the invention, monocyte differentiation is induced by pumping a blood leukocyte preparation containing monocytes through a plastic treatment apparatus. The plastic treatment apparatus used to treat the monocytes to induce monocyte differentiation may be comprised of any plastic material to which the monocytes will transiently adhere and that is biocompatible with blood leukocyte cells. Examples of materials that may be used include acrylics, polycarbonate, polyetherimide, polysulfone, polyphenylsulfone, styrenes, polyurethane, polyethylene, Teflon or any other appropriate medical grade plastic. In a preferred embodiment of the present invention, the treatment device is comprised of an acrylic plastic.

In the monocyte treatment apparatus, the leukocyte preparation flows through narrow channels. Narrow channels are used to increase the probability and frequency of monocyte contact with the interior plastic surface of the treatment apparatus. The narrow channels also result in flow patterns through the treatment apparatus which impose shearing forces to monocytes transiently contacting or adhering to the interior plastic surfaces of the treatment apparatus.

Figures 11, 12:
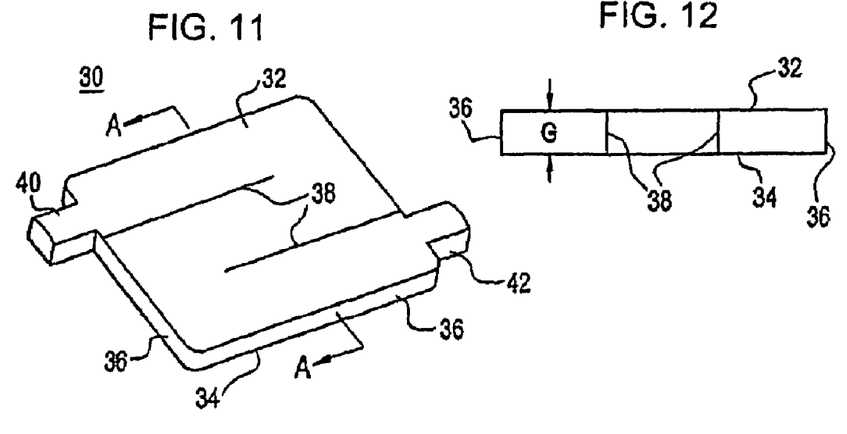
FIG. 11 is a side view of a plastic treatment apparatus which may be used to induce monocyte differentiation into functional antigen presenting dendritic cells.
FIG. 12 is a view of cross section A—A of the plastic treatment apparatus of FIG. 11.

Referring now to FIGS. 11 and 12, one embodiment of a plastic monocyte treatment apparatus is shown. In this embodiment, the treatment apparatus 30 comprises a top plate 32, a bottom plate 34 and side walls 36 to form a box-like structure having a gap, G, between the top plate 32 and the bottom plate 34 to form a narrow channel for flow of blood leukocyte preparations. The top plate 32 and the bottom plate 34 are comprised of a plastic material, such as acrylic or other suitable medical grade plastic as described above.

The side walls 36 of the treatment apparatus may be comprised of the same material as the top plate 32 and the bottom plate 34. Alternatively, the side walls 36 may be comprised of any material, such as for example a rubber, that will form a seal between with the top plate and the bottom plate. The treatment apparatus may have any desired outer shape. For example, the treatment apparatus may have rounded corners, or it may be round or oval.

The top plate 32, bottom plate 34 and side walls 36 may be fastened together using any fastening method known to those skilled in the art. For example, the top plate and bottom plate may be glued to the side walls. Alternatively, bolts, rivets or other fasteners may be used to assemble the top plate, bottom plate and side walls. Gaskets or other sealing materials may be used as necessary to seal the treatment apparatus to prevent leakage.

Internal walls 38 may be provided to direct the flow of the monocytes through the device. The internal walls are typically made of the same material as the top plate and the bottom plate. The internal walls direct the flow of the leukocyte preparation through the treatment apparatus, prevent channeling of flow through the treatment apparatus, and increase the plastic surface area that the monocytes are exposed to within the treatment apparatus. The number of internal walls and the arrangement of the internal walls may be varied to achieve the desired flow pattern through the treatment device. The available surface area may also be increased by including one or more plastic dividers or posts in the flow path through the narrow channels of the plastic treatment apparatus.

The total surface area available for monocyte interaction may also be increased by passing leukocytes through a closed plastic treatment apparatus containing plastic or metal beads. These beads increase the total surface area available for monocyte contact and may be composed of iron, dextran, latex, or plastics such as styrenes or polycarbonates. Beads of this type are utilized commercially in several immunomagnetic cell separation technologies and are typically between 0.001 and 10 micrometers in size. Unmodified beads or those coated with immunoglobulins may also be utilized in this embodiment.

Referring again to FIG. 11, the monocytes enter the treatment apparatus through an inlet connection 40, flow through the treatment apparatus and exit through an outlet connection 42. A pump (not shown) may be used to induce flow through the treatment apparatus, or the treatment apparatus may be positioned to allow gravity flow through the treatment apparatus. The inlet connection 40 and outlet connection 42 may be separate components that are fastened to the treatment apparatus, or they may be made of the same material as the treatment apparatus and formed as an integral part of the top and bottom plates or the side walls.

The top plate 32 and the bottom plate 34 are spaced apart to form a gap G that is preferably between about 0.5 mm and about 5 mm. The total volume of the treatment apparatus is preferably between 10 ml and about 500 ml but may vary depending on the application and blood volume of the mammalian species. Preferably, the leukocyte fraction is pumped through the treatment apparatus at flow rates of between about 10 ml/min and about 200 ml/min. Shearing forces are typically in the range associated with mammalian arterial or venous flow but can range from 0.1 to 50 dynes/cm$^2$. The invention is not limited in this regard, and the volume of the treatment apparatus and the flow rate of the leukocyte preparation through the treatment apparatus may vary provided that sufficient shearing forces are imposed on monocytes contacting the walls of the treatment apparatus to induce monocyte differentiation into functional dendritic cells.

The interior surfaces of the treatment device may be modified to increase the available surface area to which the monocytes are exposed. The increased surface area increases the likelihood that monocytes will adhere to the interior surface of the treatment apparatus. Also, the modified surface may influence the flow patterns in the treatment apparatus and enhance the shearing forces applied to monocytes adhered to the interior surface by the fluid flowing through the treatment apparatus. The interior surfaces of the treatment apparatus may be modified by roughening the surface by mechanical means, such as, for example, by etching or blasting the interior surfaces using silica, plastic or metal beads. Alternatively, grooves or other surface irregularities may be formed on the plastic surfaces during manufacturing. The enclosed exposure area through which the monocytes flow may also consist of a chamber whose contents include beads of various compositions to maximize surface area exposure. The invention is not limited in this regard, and the interior surface or contents of the treatment apparatus may be by any other appropriate method known to those skilled in the art.

In another embodiment of the present invention, plasma and serum proteins are removed from the blood leukocyte preparation prior to passing the leukocytes through the treatment device. Blood proteins, such as hemoglobin, albumins, etc., and cellular components such as platelets or red blood cells, can potentially adhere to the interior plastic surface of the treatment device, thereby creating a surface coating which reduces or prevents monocyte interaction with the plastic surface. By removing serum proteins from the leukocyte preparation prior to pumping the leukocyte preparation through the treatment apparatus, contamination of the plastic surfaces by plasma or serum proteins is reduced or eliminated. Reduction or elimination of this surface contamination increases the available surface area for monocyte interaction.

In this embodiment of the invention, an extracorporeal quantity of blood is treated by leukapheresis to obtain a leukocyte concentrate. The leukocyte concentrate is then further treated to remove plasma and serum proteins from the leukocyte concentrate. The serum may be separated from the leukocytes by performing an additional centrifugal elutriation, density gradient or immunoselection. Centrifugal elutriation may be carried out using a variety of commercially available apheresis devices or one specifically designed for the invention. Density gradients include, but are not limited to, Ficoll Hypaque, percoll, iodoxanol and sodium metrizoate. Immunoselection of purified monocytes may also be utilized to remove contaminating proteins and non-monocyte leukocytes prior to exposure to the device. Alternatively, the leukocyte preparation may be treated by any other method known to those skilled in the art to separate mononuclear cells from other blood components Following removal of serum or plasma components, the leukocyte preparation is pumped through a plastic monocyte treatment apparatus as described above to induce monocyte differentiation into dendritic cells. After the leukocyte preparation is pumped through the treatment apparatus, it is incubated for an appropriate period of time to allow the treated monocytes to differentiate into functional dendritic cells. During this time, immature dendritic cells may be loaded with exogenous antigens including those from whole cells, proteins or peptides. The treated monocytes are typically incubated for a period of between about 12 hours and about 36 hours.

The efficacy of the methods described above are demonstrated by the data shown in FIGS. 13 and 14. This data was obtained using a small plastic treatment apparatus to treat samples of peripheral blood containing monocytes. The treatment apparatus used in these tests had acrylic top plates and bottom plates which were bolted together. The treatment apparatus had a single channel of 30 by 3 cm dimension, 1 mm interplate gap and a total void volume of approximately 10 ml. The leukocyte concentrate was pumped through the treatment apparatus at a flow rate of about 50 ml/minute for 30 minutes. The treated cells incubated overnight to allow differentiation of monocytes into functional dendritic cells.

Figure 13:
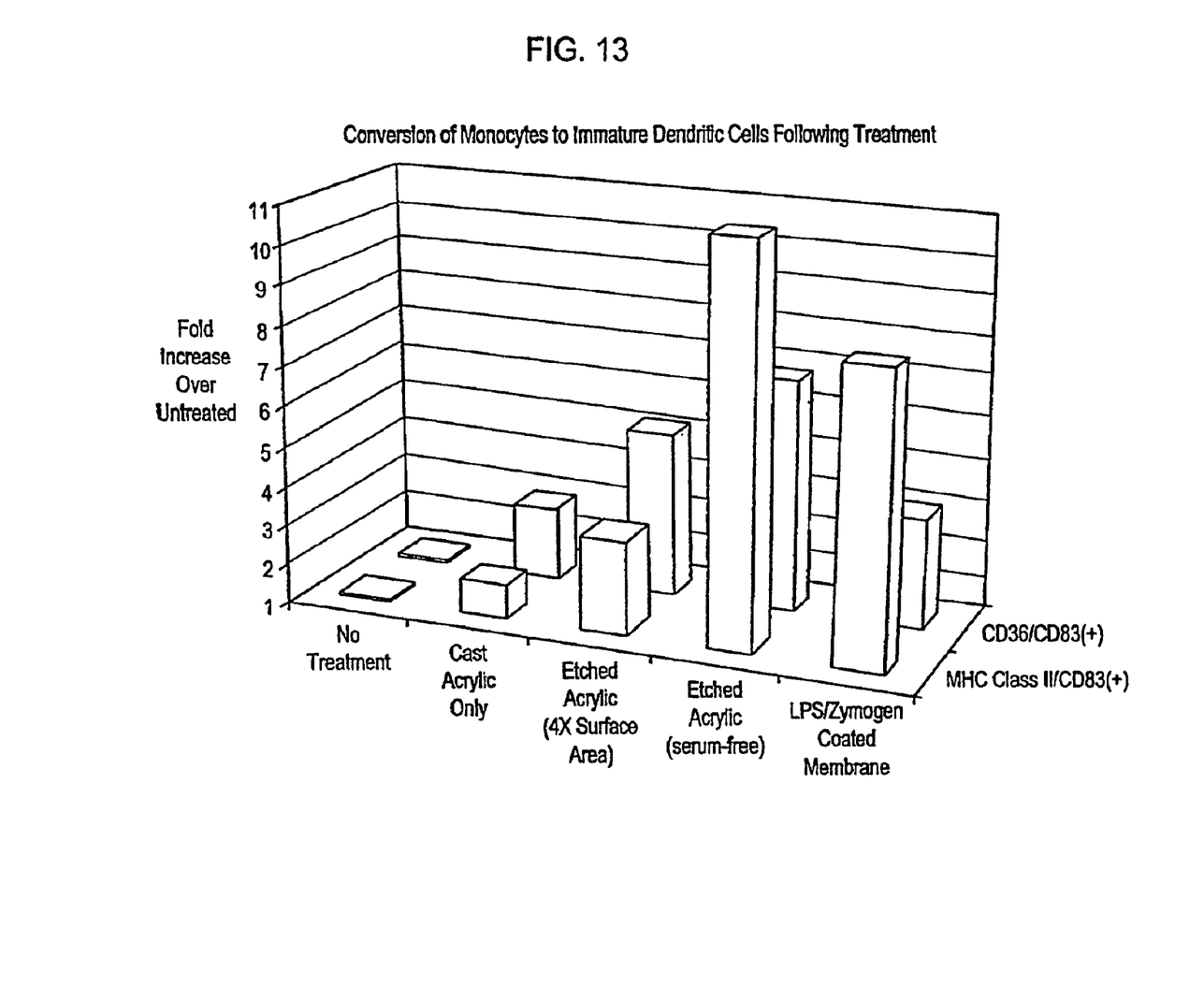
FIG. 13 is a bar chart showing the increase in immature dendritic cells as indicated by the cell markers CD36/CD38 and MHC Class II/CD83 in samples of blood treated in a cast acrylic device, in an etched acrylic device (4× surface area), in an etched acrylic device (4× surface area) serum free, and using a LPS/Zymogen coated membrane.
Figure 14:
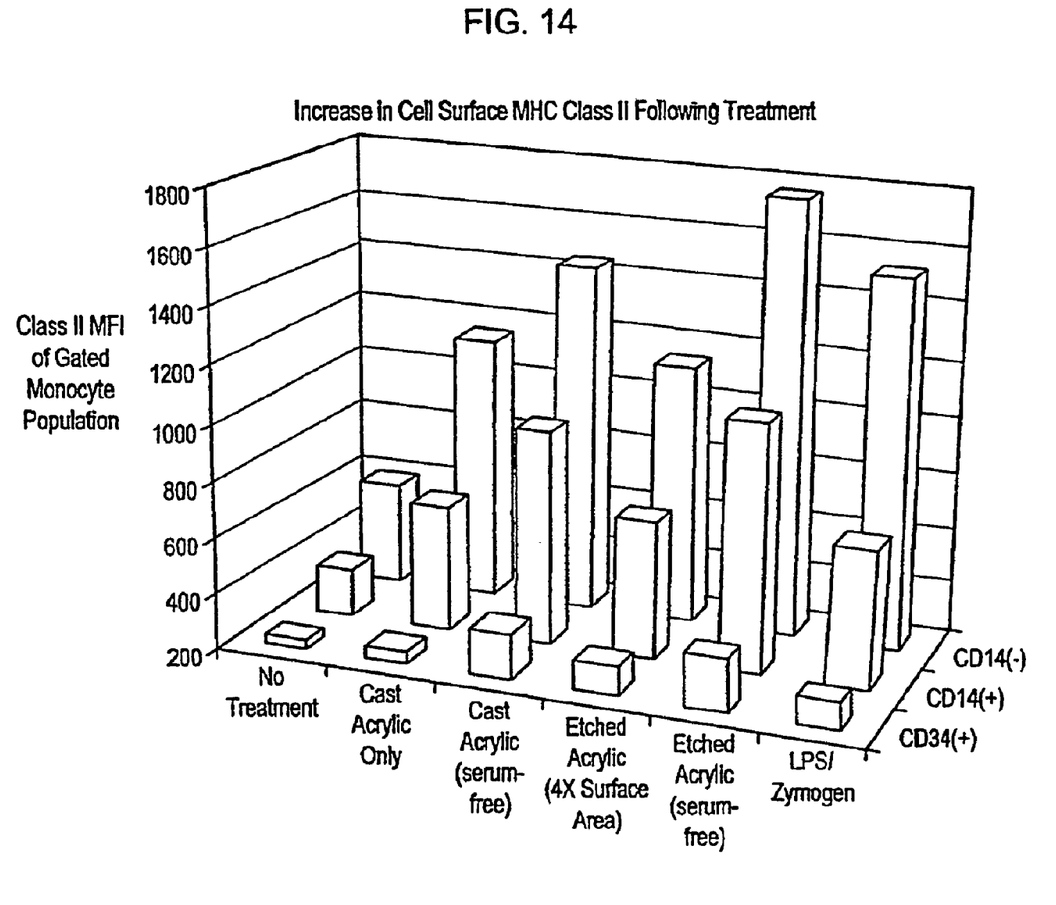
FIG. 14 is a bar chart showing the increase in the cell surface MHC Class II cell markers in samples of blood treated in a cast acrylic device, in an etched acrylic device (4× surface area), in an etched acrylic device (4× surface area) serum free, and using a LPS/Zymogen coated membrane.

The data illustrated in FIGS. 13 and 14 was obtained by treating peripheral blood in (1) a treatment apparatus having an unmodified cast acrylic panel; (2) a treatment apparatus having an acrylic panel etched with silica beads to increase the surface area of the panel by a factor of approximately four; and (3) a treatment apparatus having an etched acrylic panel and serum-free peripheral blood monocytes (PBMC) isolated over Ficoll Hyplaque. The conversion of blood monocytes to immature dendritic cells was measured by using previously established markers of dendritic cell development, including cell surface MHC class II and CD36 and intracellular production of CD83.

As shown in FIGS. 13 and 14, treatment of peripheral blood in a cast acrylic treatment apparatus approximately doubled the population of immature dendritic cells in the samples as compared to untreated blood. When the interior surface of the acrylic treatment apparatus was etched to increase the surface area, treatment of the peripheral blood approximately tripled the population of immature dendritic cells as compared to untreated blood. Treatment of peripheral blood with the serum removed prior to treatment increased the population of dendritic cells by a factor of up to eight as compared to untreated blood.

These results demonstrate that treatment of peripheral blood monocytes by pumping the monocytes through a plastic treatment apparatus having narrow channels is an effective method of inducing monocyte differentiation into functional dendritic cells. Etching the surface of the treatment apparatus and removing plasma and serum from the peripheral blood being treated can further enhance the population of dendritic cells obtained.

In another embodiment of the present invention, PBMC are pumped through a treatment apparatus similar to that described above, with at least one interior surface of the treatment apparatus comprises a nylon membrane coated with the inflammatory molecules LPS and Zymogen. As the monocytes in the peripheral blood flow through the treatment apparatus, the monocytes are exposed to these proteins. The stimulatory surface interaction between the LPS/Zymogen and the monocytes induces monocyte differentiation into functional dendritic cells. As shown in FIG. 15, the dendritic cell population in peripheral blood samples treated by exposing the monocytes to an LPS/Zymogen coated membrane is comparable to the increase population observed by treatment of a serum-free blood in an etched acrylic treatment apparatus. It will be recognized that this embodiment of the invention is not limited to use of LPS and Zymogen, the treatment apparatus may include any protein that can be crosslinked to solid supports such as nylon membranes or plastic surfaces and will interact with blood monocytes to induce differentiation into functional dendritic cells. Proteins which can be absorbed to solid supports and used to induce monocyte differentiation include, but are not limited to, inflammatory molecules, adhesion molecules, cytokines, chemokines or serum proteins known to affect leukocyte adhesion and activation.

The dendritic cells formed by the methods described above can be co-incubated with apoptotic or inactivated disease effector agents as described below. The dendritic cells will phagocytize the apoptotic or inactivated disease effector agents and present antigens from the disease effector agents at the surface of the dendritic cells. These antigen loaded dendritic cells can then be administered for immunotherapeutic treatment. Alternatively, the dendritic cells can be frozen for later use in immunotherapeutic treatments.

In another embodiment of the present invention, in order to bring the induced dendritic cells into physical contact with malignant cells, an extracorporeal quantity of blood may be treated using a plastic treatment apparatus to induce monocyte differentiation, and the treated monocytes may be reintroduced to the subject without overnight incubation. This approach may be preferable in certain clinical situations involving solid tumors, in which the target tumor is localized in a particular organ, either as a primary cancer of that organ or as a metastasis. Apoptosis or necrosis of a percentage of the malignant cells in such a site can be readily induced by established methods known to those skilled in the art, such as for example localized radiotherapy or transient blockage of the local arterial supply or local introduction of chemotherapy. The new dendritic cells, induced from monocytes treated extracorporeally by passing the monocytes through plastic channels using the methods described above, can then be introduced into the relevant tumor site through the blood supply, thereby bringing the dendritic cells into contact with apoptotic or necrotic tumor cells, which are internalized, processed and presented by the dendritic cells. The tumor antigens processed and presented in this manner can then initiate anti-tumor immunity, when the tumor-loaded dendritic cells stimulate relevant anti-tumor T cell responses. In circumstances in which immature dendritic cells can lead directly to tumor cell destruction, the induced dendritic cells can alternatively be introduced to the tumor site via the blood supply without prior damage to the malignant tumor.

Among the advantages of this embodiment of the invention are that the treatment time is reduced, as no incubation is required after treatment of the extracorporeal quantity of blood, and there is no need to remove or treat tumor cells ex vivo to induce apoptosis or cell death. If desired, the treatment can be combined with radiation or chemotherapeutic treatments in one procedure, thereby reducing the number of times a particular subject must appear for treatment.

Protocol and Clinical Results of Application of the Invention

An example of the application of the present invention will be described with particular reference to an enhanced therapy for treating cutaneous T-cell lymphoma. However, it should be understood that the invention is not limited to this particular application and that the invention may be employed to treat any disease state which includes as a component disease effector agents distinguishable by their own surface antigens. A number of such disease states, component effector agents and disease associated antigens have been discussed above.

Cutaneous T-cell lymphoma (CTCL) is an immune disease that is caused by a massive expansion of a single clone of aberrant T-cells. These malignant cells are distinguished by clone-specific or tumor-specific cell surface antigens, at least one set of which are derived from clone specific protein components of the clone-specific T-cell receptor. Cytotoxic T-cell responses can be generated selectively against these clone-specific antigens. During the past decade, photopheresis has become a standard immunotherapy for advanced CTCL and works, at least in part, by generating such anti-CTCL immune responses. In standard CTCL treatment using photopheresis, leukocytes and monocytes are separated by leukapheresis from an extracorporeal quantity of a subject's blood. The monocytes and leukocytes are circulated through an ultraviolet A exposure system of the type described above, in which biologically inert 8-MOP is activated to covalently bond to DNA and cytoplasmic proteins in the malignant lymphocytes. This is a highly directed therapy, since the drug remains active for only millionths of a second, thereby chemically altering only those cells in the exposure field and explaining the paucity of systemic side effects. Photopheresis provides increased immunogenicity of the exposed leukocytes, without causing general immunosuppression. Thus, returning the treated cells to the subject can lead to a "vaccination" effect which, in the most responsive subjects, results in a sustained immunologic response to the chemically altered and reintroduced leukocytes. Alteration and return of less than 5% of the body burden of malignant T-cells can induce a meaningful anti-tumor response which in some subjects has resulted in complete remissions lasting more than fifteen years. Methods for applying photopheresis to the treatment of CTCL are disclosed in U.S. Pat. Nos. 5,114,721 and 4,838,852 and published PCT applications WO 97/34472 and WO 94/11016, the disclosures of which are incorporated herein by reference.

The clinical results achieved through the application of photopheresis to CTCL have encouraged a search for the treatment's underlying mechanism for two major reasons. First, if the mechanism by which photopheresis vaccinates patients against their malignant cells could be better understood, it should then be possible to refine the methodology and enhance its efficacy. For example, only 25% of the patients with advanced CTCL have a major persistent response to photopheresis. While these positive responses are profound and their frequency exceeds those produced by prior conventional chemotherapy, it would be desirable to increase the efficiency of the procedure. Second, if the mechanism could be better understood, it should then also be possible to extend the revised therapy to other types of malignancies and disease processes. This application is based on the new recognition of the role of dendritic antigen presenting cells in the response to photopheresis, and more particularly on methodology of enhancing this role. Studies in experimental systems and with transformed human cells lines have yielded four lines of evidence. First, the treatment stimulates CD8 T-cells to suppress the activity of pathogenic clones of T-cells. Second, these CD8 cells, at least in CTCL where there is only a single clone of pathogenic T-cells, recognize tumor-specific peptide antigens in the context of Class I MHC complexes at the tumor cell surface. Third, exposure of human lymphoblasts to photo-activated 8-MOP triples the display of Class I complexes, peaking after overnight incubation. Finally, the treatment also causes apoptosis in lymphocytes and their ingestion by phagocytic mononuclear cells.

Multiple lines of clinical and experimental evidence have confirmed the "vaccination" phenomenon which is associated with the induction of potent CD8 responses capable of selectively suppressing aberrant T-cell populations. In the case of CTCL, at least some of the anti-cancer CD8 T-cells selectively targeted tumor-specific peptides derived from the T-cell receptor proteins of the malignant cells. Since the T-cell receptors of CD8 T-cells recognize antigenic peptides in the context of Class I MHC, attention has focused on the impact of 8-MOP on the display of these complexes. It has recently been reported that 8-MOP triples the display of Class I MHC at the cell surface of transformed human lymphocytes, maximizing about 22 hours after exposure, and that this effect is dependent on the degradation of cytoplasmic proteins and the transport of the generated peptide fragments across the endoplasmic reticulum through TAP pores. This effect appears to be initiated by binding of 8-MOP to aromatic amino acids of cytosolic proteins rather than the drug's other main molecular target, pyrimidine bases of DNA.

The present invention is based on the assumption that if an immune response is to be generated against weakly immunogenic complexes containing the relevant antigens, then such a response might be maximized if the complexes are maximized on the antigen presenting cells. In conventional photopheresis, T-cells are immediately returned to the subject at a point when apoptosis is only modestly elevated over baseline and when Class I complexes are also only modestly enhanced. In the present method, the treated leukocytes are incubated overnight, typically for a period of from about 6 to 48 hours. An unexpected finding was that overnight incubation of the treated cells not only enhances the expression of Class I complexes by the apoptotic T-cells, but also maximized the maturation of monocytes into functional dendritic cells. Thus, the convergence of these two phenomena made the incubation phase a simple means of bringing large numbers of apoptotic malignant cells into apposition with increased numbers of functional dendritic cells capable of ingesting apoptotic cells or fragments of apoptotic cells. It has previously been shown the mononuclear cells in the photopheresis bag have already begun to phagocytose apoptotic T-cells, although these mononuclear cells do not have the properties of dendritic cells. Typically, antigen presenting cells process endocytosed antigens through the Class II MHC pathway, which ordinarily stimulates expression of CD4T-cells rather than the desired CD8 cytoxic cells which "see" antigens only in the context of Class I MHC. However, it is important to note that it has recently been reported that dendritic cells have a special capacity to process and present antigens derived from apoptotic cells through the Class I MHC system.

An enhanced photopheresis protocol based on the present invention has provided encouraging clinical results in a pilot study which included four subjects suffering from advanced CTCL. However, before discussing the clinical results of the study, a treatment protocol describing an embodiment of the present invention will be set forth in the following examples.

Photopheresis Protocol

The first step, which is the photopheresis protocol, is essentially the same as the protocols currently approved by the FDA. Subjects receive either oral 8-MOP (0.6 mg/kg) or intravenous 8-MOP directly into the photopheresis apparatus, to yield a concentration of 50–200 ng/ml of drug. Next, the blood is leukapheresed to obtain a buffy coat and is then passed through a contiguous closed circuit ultraviolet A exposure device, which delivers about 1–2 joules/cm$^2$ of ultraviolet A energy (320 nm–400 nm). In this manner, about 1 to 100 molecules of 8-MOP are induced to covalently bind to each million base pairs of DNA. A nearly equal amount of 8-MOP is induced to covalently bind to aromatic amino acids of cytoplasmic proteins. The treated leukocyte fraction, comprising a total volume of approximately 250 cc, is combined with 500 cc saline and then sequestered in a standard blood bank bag, as is typical for the photopheresis procedure. Following photopheresis, the treated fraction is subjected to the following novel incubation phase protocol.

Incubation Phase Protocol

Following collection of the post photopheresis sample after ultraviolet A activation with 8-MOP, the treated cell populations are incubated as follows:

1. Remove two Amicus platelet storage bags (Baxter Fenwall PL 2410) from an apheresis kit (Baxter Fenwall 4R 23-12) by heat sealing the tubing and cutting the tubing at the end connecting to the kit.

2. Insert a sharp catheter into the pheresis bag (spike), thereby breaking the seal, with a Charter Medical 3-leg transfer set (#O3-220-02) and clamp the tubing. Spike the two Amicus bags with the other piercing pins of the same transfer set thereby establishing a passageway for the transfer of the cell suspension.

3. Hang the pheresis bag on an IV pole and open the clamp allowing ½ of the pheresis to drain into each Amicus bag by gravity, and then clamp the tubing.

4. Remove the spikes and replace with sampling site couplers.

5. Place each Amicus bag in a separate Fenwall centrifuge bag and into a centrifuge carrier.

6. Centrifuge for 10 minutes, at 1000 rpm, 23° C., to concentrate the cells as a pellet at the bottom of each bag to permit removal of a large fraction of the plasma, which contains traces of plasticizer.

7. After centrifugation, insert a needle attached to the tubing on a transfer pak into the sampling coupler on one of the Amicus bags.

8. Carefully place the Amicus bag in a plasma extractor to avoid resuspending the cell pellet. Close the extractor and express the plasma into the transfer bag by slowly tipping the extractor forward. When approximately 50 cc has drained into the transfer bag and/or the pellet begins to resuspend, return the extractor to an upright position and remove the needle.

9. Remix the contents of the bags by gentle agitation being careful to resuspend any adherent cells attached to the bag wall.

10. Spike one 500 cc bottle containing 100 cc of colorless RPMI 1640 media with Hepes Buffer with a Baxter vented medication set and clamp the tubing. Insert the attached needle into the sampling coupler port on the first Amicus bag. Hang the bottle on the IV pole and open the tubing allowing the media to drain into the bag.

11. Clamp the tubing and remove the needle and discard the medication set. Mix the bag by gentle inversion and place the bag in a 370° C. incubator on a shelf with the Abel side down, overnight.

12. Repeat steps 8–12 for the second bag.

13. Following incubation for a period of 6–24 hours, remove one bag from the incubator, gently mix by agitation and inversion, making sure that all adherent cells are resuspended. Take out 60 cc of blood in a syringe. Inject one aerobic, and one anaerobic blood culture bottle for microbiology. Inject one lavender top tube for WBC and differential to be sent to hematology.

14. Resuspend the second Amicus bag and place both bags in individual centrifuge bags and centrifuge.

15. Remove and transfer the supernatant fluid as described in steps 8–10.

16. Return well mixed blood to the patient.

Figure 1:
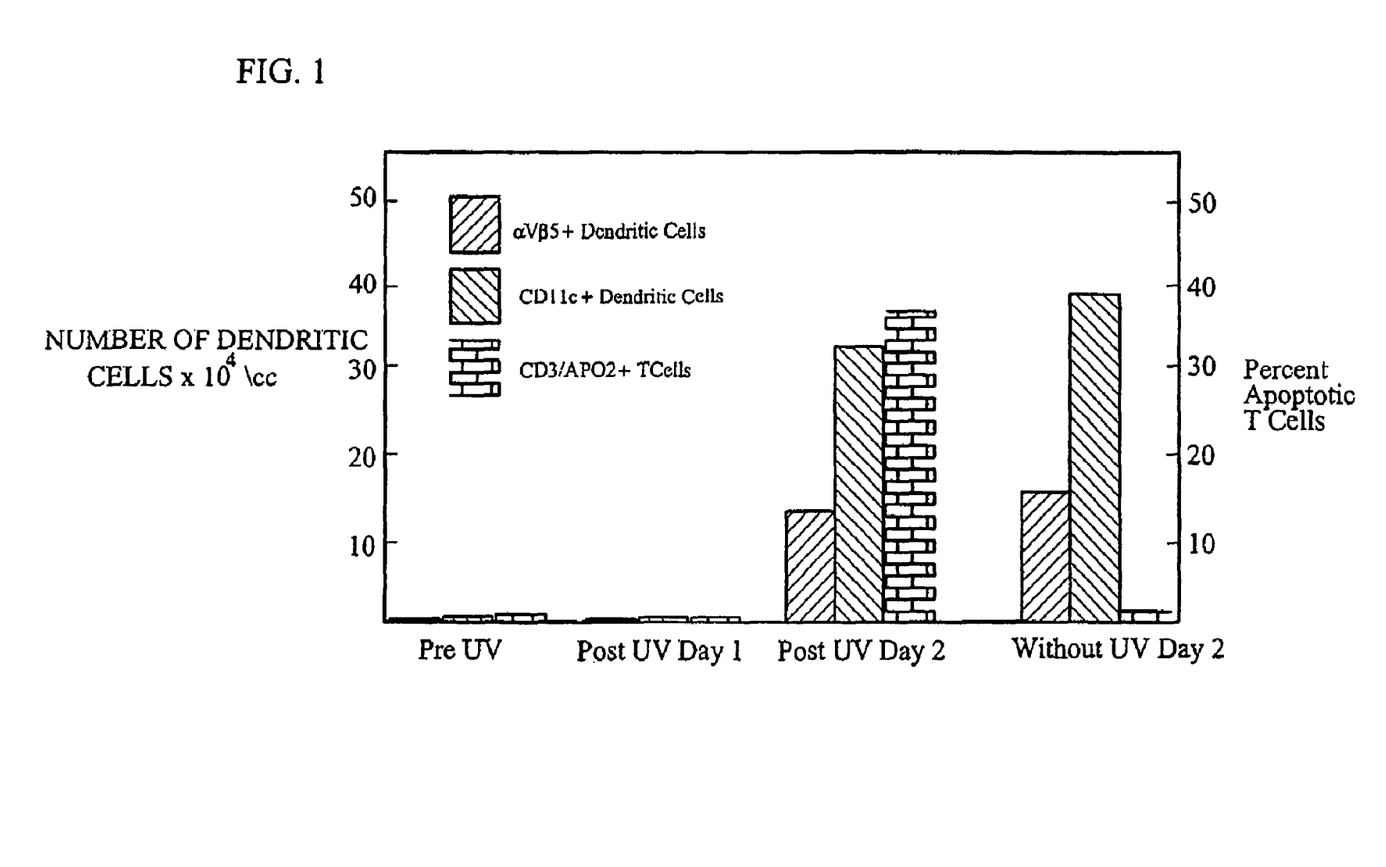
FIG. 1 is a graph which illustrates the generation of both dendritic antigen presenting cells and apoptotic T-cells following overnight incubation of blood exposed to 8-MOP and ultraviolet A energy.

FIG. 1 is a composite graph which illustrates the generation of both dendritic antigen presenting cells and apoptotic T-cells following treatment by the photopheresis and incubation protocols set forth above. As shown in FIG. 1, pre-treatment blood contained nearly undetectable numbers of dendritic cells, using either the αVβ5 or CD11c markers for identification. After incubation for about 22 hours, both of these markers revealed large numbers of mature dendritic cells. Similarly, the pre-treated blood contained very few apoptotic T-cells. Only after overnight incubation did apoptotic T-cells become significantly evident, as illustrated by the simultaneous identification of the T-cells with the CD3 marker and the apoptotic cells with the APO2 markers.

The fourth set of bars at the far right of the graph illustrates the differentiation of monocyte into mature dendritic cell by means of physical perturbation and incubation only, without exposure to ultraviolet light. Differentiation was initiated by isolating monocytes and T-cells from an extracorporeal quantity of blood by leukapheresis. The isolated monocytes and T-cells were not subjected to photopheresis but were exposed only to the centrifugal forces associated with leukapheresis. The isolated cell populations were then incubated for a period of about 22 hours according to the incubation protocol set forth above. As shown in FIG. 1, the physical forces applied during leukapheresis, together with overnight incubation, caused the monocytes to efficiently evolve into functional dendritic cells, as identified by the αVβ5 and CD11c markers. No significant apoptosis of the T-cells was observed, indicating that treatment with 8-MOP followed by exposure to UV, or some other form of treatment as described above, is required to induce T-cell apoptosis.

The Y axis of the graph gives the number of functional dendritic cells per cubic centimeter. Since the total volume incubated over the 22 hour period was 250 cc, 32.5 million dendritic cells (130,000×250) were generated, as indicated in the third set of bars by the CD11c marker. It has been shown that dendritic cells having this level of maturity phagocytose apoptotic cells and are efficient presenters of antigens derived from such cells. Monocytes may also ingest apoptotic cells or fragments of such cells, but monocytes cannot efficiently present antigen material processed from the apoptotic cells to CD8 cytoxic T cells. CD8 T cells only recognize antigens which are associated with Class I MHC at the surface of the antigen presenting cell. Monocytes primarily present antigens derived from ingested cells in association with Class II MHC molecules, which CD8 T cells cannot recognize. Dendritic cells, on the other hand, in part because they include the αVβ5 integrin, have the special ability to "cross-prime" CD8 T cells by presenting the antigens derived from the digestion of apoptotic cells and displaying the processed antigens in association with the Class I MHC molecules that CD8 cytoxic T cells can recognize. This is a major reason why functional dendritic cells are so useful in stimulating tumor immunity, or suppressing undesirable immunologic processes by attacking the aberrant T cells that cause them.

The graph illustrated in FIG. 1 further demonstrates an effective means of determining the optimum incubation time for the mixed cell populations. Since the particular markers employed permit the numbers of dendritic cells and apoptotic T-cells to be quantified simultaneously, the incubation time that results in the optimal combination of apoptotic cells and newly formed dendritic cells can be readily determined. This is the controlling determinant establishing when to terminate incubation and reinfuse the incubated cells into the subject.

As noted previously, an incubation time of from about 12 to about 48 hours results in a maximum number of dendritic cells. The apoptotic T-cells maximize in a period of about 6 to about 40 hours. Accordingly, an incubation period of from about 6 to about 24 hours provides the most advantageous combination of apoptotic T-cells and dendritic cells. After an incubation period of this duration, the number of apoptotic cells is at a maximum and large numbers of functional dendritic cells are also present in the incubation bag. Thus, a maximum number of apoptotic cells capable of expressing disease-associated antigens are present and a large number of functional dendritic cells capable of processing and presenting those antigens are also present. In the case where the disease effector agent is derived from an exogenous source and is added to the incubation bag, the incubation period required for maximizing the number of apoptotic cells is obviously not a factor. In such instances, the time period required for maximizing the number of induced dendritic cells is the factor which determines the duration of the co-incubation.

Clinical Efficacy of Combined Treatment and Co-Incubation

The treatment method taught by the present invention has been tested in a pilot study involving four CTCL subjects whose disease had been advancing while on standard photopheresis. The four patients in the pilot study were carefully selected from a large CTCL population based on three criteria: (1) increasing tumor burden despite continued conventional photopheresis; (2) malignant clones that could be quantified in blood; and (3) low absolute blood CD8 levels. The leukemic cells in three of the subjects could readily be distinguished from normal T-cells, since their clonal T-cell receptor phenotype was recognizable using fluorescein-tagged anti-family V T-cell receptor monoclonal antibodies (V mAb). Values above 5% indicate expansion of the malignant clone. Although the clonal T-cell receptor of the fourth patient's CTCL cells does not bind any currently available V mAb, the CD4/CD8 ratio permits quantification of that patient's leukemic population as well. The unresponsiveness of the four patients to conventional photopheresis likely reflects their CD8 T cell deficiency, since clinical responders usually require an intact CD8 compartment. Therefore, these patients present a significant challenge for the new treatment approach. Although the study population was small, it was easy to quantify reversal of disease progression in this poor prognosis patient group.

Following treatment with the above-described protocol, each of the four patients had a diminution in the absolute circulating malignant pool over the twelve months of the protocol. Whereas none experienced complete hematologic remission, the previous rapid increases in blood CTCL cells were reversed. Those symptomatic infections common in individuals whose immune systems have been compromised by their CTCL, and the therapy for this disease, were not encountered. Measurements of tumor burden and clinical response centered on blood determinations and quantitation of the number of infiltrating T cells in biopsies of the clinically most severe skin lesions. It is important to note that the severity and distribution of skin lesions in three of the four patients lessened. In one patient, long-standing, maximal, generalized exfoliative erythroderma associated with intractable pruritus was transformed to low grade, nearly asymptomatic erythroderma, and two of the other patients had nearly complete cutaneous remissions.

The photopheresis/incubation protocol tested in this study, like conventional photopheresis, appears to be safe, since no side effects were encountered in these subjects. Further, the capacity of the protocol to bring together malignant apoptotic cells bearing the relevant immunizing antigens with functional dendritic cells capable of presenting these antigens to a responding immune system offers additional opportunities for immunotherapy beyond the treatment of CTCL. For example, in a recently reported randomized, controlled trial, the combination of photopheresis with conventional immunosuppressive drugs proved effective in reducing the number of rejection episodes experienced by heart transplant recipients. Preliminary, studies have also suggested the efficacy of conventional photopheresis in certain autoimmune diseases, such as rheumatoid and psoriatic arthritis, lupus erythematosus, scleroderma and graft-versus-host disease (following allogeneic bone marrow transplantation). The present invention's capacity to provide an in vivo source of large numbers of dendritic cells should enhance these therapies. Modifications to the protocol may also permit co-cultivation of dendritic cells derived from induced monocytes with suspended apoptotic solid tumor cells, apoptotic infectious microbes or inactivated or incomplete viruses.

Accordingly, it should be understood, as noted above, that while certain aspects of the invention has been described in connection with an enhanced therapy for CTCL, the invention is applicable to a broad range of immune diseases without departing from the spirit and scope of the invention.

We claim:

1. A method for inducing differentiation of monocytes contained in an extracorporeal quantity of a mammal's blood into functional dendritic cells, said method comprising the steps of:
   (a) treating the extracorporeal quantity of blood to obtain a leukocyte concentrate containing monocytes;
   (b) treating the leukocyte concentrate to reduce the quantity of plasma and serum proteins in the leukocyte concentrate;
   (c) treating the leukocyte concentrate to induce differentiation of the monocytes contained in the leukocyte concentrate into functional dendritic cells by pumping the leukocyte concentrate through a treatment apparatus having at least one plastic channel at a suitable flow rate to apply a shearing force to monocytes adhering to the walls of the at least one plastic channel; and (d) incubating the treated leukocyte concentrate for a sufficient period of time to allow the monocytes contained in the treated leukocyte concentrate to differentiate into functional dendritic cells.

2. The method of claim 1, wherein the step of treating the extracorporeal quantity of blood to obtain a leukocyte concentrate containing monocytes comprises centrifugal elutriation of the blood.

3. The method of claim 2, wherein the step of treating the leukocyte concentrate to reduce the quantity of plasma and serum proteins in the leukocyte concentrate comprises performing a second centrifugal elutriation on the leukocyte concentrate.

4. The method of claim 3, wherein the leukocyte concentrate is treated to remove substantially all plasma and serum proteins from the leukocyte concentrate.

5. The method of claim 1, wherein the treatment apparatus comprises a plastic selected from the group consisting of acrylics, polycarbonate, polyetherimide, polysulfone, polyphenylsulfone, styrenes, polyurethane, polyethylene and Teflon.

6. The method of claim 5, wherein the surface of the plastic channel exposed to the leukocyte concentrate is mechanically treated to increase the surface area.

7. The method of claim 6, wherein the mechanical treatment comprises blasting the surface of the plastic channel with beads.

8. The method of claim 7, wherein the beads comprise a material selected from the group consisting of silica, plastic or metal.

9. The method of claim 2, wherein the step of treating the leukocyte concentrate to reduce the quantity of plasma and serum proteins in the leukocyte concentrate comprises treating the leukocyte concentrate using a density gradient.

10. The method of claim 2, wherein the step of treating the leukocyte concentrate to reduce the quantity of plasma and serum proteins in the leukocyte concentrate comprises treating the leukocyte concentrate by immunoselection.

11. The method of claim 1, wherein the treated leukocyte concentrate is incubated for a period of between about 12 hours to about 36 hours.

12. The method of claim 1, wherein the treatment apparatus comprises a rectangular top plate fixedly attached to a plurality of side walls;
a bottom plate fixedly attached to the plurality of side walls opposite the top plate;
an inlet connection fixedly attached to one side wall wherein the inlet connection allows fluids to flow into the treatment apparatus; and
an outlet connection fixedly attached to a second side wall wherein the outlet connection allows fluids to flow out of the treatment apparatus.

13. The method of claim 12, wherein the top plate and the bottom plate of the treatment apparatus are spaced apart at a distance of between about 0.5 mm and about 5 mm.

14. The method of claim 12, wherein the treatment apparatus has a volume of between about 10 ml and about 500 ml.

15. The method of claim 1, wherein the leukocyte concentrate is pumped through the treatment apparatus at a flow rate of between about 10 ml/min and about 200 ml/min.

16. The method of claim 1, wherein the leukocyte concentrate is pumped through the treatment apparatus to induce shearing forces of between about 0.1 dyne/cm$^2$ to about 50 dynes/cm$^2$ on monocytes adhering to the walls of the at least one plastic channel.

17. A method for inducing differentiation of monocytes contained in an extracorporeal quantity of a mammal's blood into functional dendritic cells, said method comprising the steps of:

(a) treating the extracorporeal quantity of blood to obtain a leukocyte concentrate containing monocytes;

(b) treating the leukocyte concentrate to induce differentiation of the monocytes contained in the leukocyte concentration into functional dendritic cells by pumping the leukocyte concentrate through a treatment apparatus having at least one surface comprising a nylon membrane with protein molecules cross-linked to the nylon membrane wherein a stimulatory surface interaction occurs between the monocytes and the proteins; and (c) incubating the treated leukocyte concentrate for a sufficient period of time to allow the monocytes contained in the treated leukocyte concentrate to differentiate into functional dendritic cells.

18. The method of claim 17 wherein the protein molecules are selected form the group consisting of inflammatory molecules, adhesion molecules, cytokines, chemokines or serum proteins.

19. The method of claim 18 wherein the protein molecules are lipopolysaccharide and zymogen.

20. A method for inducing an immune response to tumor cells in a mammal comprising the steps of:

(a) treating the subject to induce cell death of a plurality of tumor cells in vivo;

(b) treating an extracorporeal quantity of blood from the subject to obtain a leukocyte concentrate containing monocytes;

(c) treating the leukocyte concentrate to reduce the quantity of plasma and serum proteins in the leukocyte concentrate;

(d) treating the leukocyte concentrate to induce differentiation of the monocytes contained in the leukocyte concentrate into functional dendritic cells by pumping the leukocyte concentrate through a treatment apparatus having at least one plastic channel at a suitable flow rate to apply a shearing force to monocytes adhering to the walls of the at least one plastic channel; and (e) administering the treated leukocyte concentrate to the subject.

21. The method of claim 20, wherein the subject is treated by at least one of radiation therapy or chemotherapy to induce the death of a plurality of tumor cells in vivo.

22. The method of claim 20, wherein the step of treating the extracorporeal quantity of blood to obtain a leukocyte concentrate comprises centrifugal elutriation of the blood.

23. The method of claim 22, wherein the step of treating the leukocyte concentrate to reduce the quantity of plasma and serum proteins in the leukocyte concentrate comprises performing a second centrifugal elutriation on the leukocyte concentrate.

24. The method of claim 23, wherein the leukocyte concentrate is treated to remove substantially all plasma and serum proteins from the leukocyte concentrate.

25. The meted of claim 20, wherein the treatment apparatus comprises a plastic selected from the group consisting of acrylics, polycarbonate, polyetherimide, polysulfone, polyphenylsulfone, styrenes, polyurethane, polyethylene and Teflon.

26. The meted of claim 25, wherein the surface of the plastic channel exposed to the leukocyte concentrate is mechanically treated to increase to increase the surface area.

27. The method of claim 26, wherein the mechanical treatment comprises blasting the surface of the plastic channel with beads.

28. The method of claim 27, wherein the beads comprise a material selected from the group consisting of silica, plastic or metal.

29. The method of claim 22, wherein the step of treating the leukocyte concentrate to reduce the quantity of plasma and serum proteins in the leukocyte concentrate comprises treating the leukocyte concentrate using a density gradient.

* * * * *